United States Patent
Zanardi et al.

(10) Patent No.: US 11,234,997 B2
(45) Date of Patent: Feb. 1, 2022

(54) ANTIBACTERIAL ACTIVITY OF GALACTOOLIGOSACCHARIDE AND XYLITOL IN DERMATOLOGICAL TREATMENTS

(71) Applicant: ROTTAPHARM SPA, Monza (IT)

(72) Inventors: Andrea Zanardi, Milan (IT); Alessandra Cercaci, Rivalta di Torino (IT); Ivan Montaldo, Castagnito (IT)

(73) Assignee: Rottapharm SpA

( * ) Notice: Subject to any disclaimer, the term of this patent is extended or adjusted under 35 U.S.C. 154(b) by 0 days.

(21) Appl. No.: 16/624,978

(22) PCT Filed: Jun. 27, 2018

(86) PCT No.: PCT/EP2018/067337
§ 371 (c)(1),
(2) Date: Dec. 20, 2019

(87) PCT Pub. No.: WO2019/002421
PCT Pub. Date: Jan. 3, 2019

(65) Prior Publication Data
US 2020/0171070 A1   Jun. 4, 2020

Related U.S. Application Data

(60) Provisional application No. 62/525,489, filed on Jun. 27, 2017.

(51) Int. Cl.
| | | |
|---|---|---|
| A61K 31/715 | (2006.01) | |
| A61K 31/047 | (2006.01) | |
| A61K 31/702 | (2006.01) | |
| A61K 8/06 | (2006.01) | |
| A61K 8/34 | (2006.01) | |
| A61K 8/60 | (2006.01) | |
| A61K 9/00 | (2006.01) | |
| A61K 9/06 | (2006.01) | |
| A61K 9/107 | (2006.01) | |
| A61P 17/00 | (2006.01) | |
| A61P 31/04 | (2006.01) | |
| A61P 17/16 | (2006.01) | |
| A61K 8/73 | (2006.01) | |
| A61Q 17/00 | (2006.01) | |
| A61Q 19/00 | (2006.01) | |
| A61Q 19/10 | (2006.01) | |

(52) U.S. Cl.
CPC ............ *A61K 31/715* (2013.01); *A61K 8/062* (2013.01); *A61K 8/345* (2013.01); *A61K 8/60* (2013.01); *A61K 8/73* (2013.01); *A61K 9/0014* (2013.01); *A61K 9/06* (2013.01); *A61K 9/107* (2013.01); *A61K 31/047* (2013.01); *A61K 31/702* (2013.01); *A61P 17/00* (2018.01); *A61P 17/16* (2018.01); *A61P 31/04* (2018.01); *A61Q 17/005* (2013.01); *A61Q 19/00* (2013.01); *A61Q 19/10* (2013.01); *A61K 2800/592* (2013.01)

(58) Field of Classification Search
CPC .. A61K 31/715; A61K 31/047; A61K 31/702; A61K 9/06; A61K 9/107; A61K 8/062; A61K 8/73; A61K 8/345; A61K 8/60; A61K 9/0014; A61K 2800/592; A61P 17/00; A61P 31/04; A61P 17/16; A61Q 19/00; A61Q 19/10; A61Q 17/005
USPC ......................................................... 514/54
See application file for complete search history.

(56) References Cited

U.S. PATENT DOCUMENTS

2015/0202136 A1   7/2015   Lanzalaco et al.
2017/0281660 A1 * 10/2017   Zapka .................. A61K 31/702

FOREIGN PATENT DOCUMENTS

| CN | 103462881 A | 12/2013 |
|---|---|---|
| CN | 104970176 A | 10/2015 |
| CN | 105796377 A | 7/2016 |
| CN | 106071033 A | 11/2016 |
| CN | 106616602 A | 5/2017 |
| WO | 2008148694 A1 | 12/2008 |
| WO | 2013122931 A2 | 8/2013 |

OTHER PUBLICATIONS

Marini et al. Pre- and probiotics for human skin. Handbook of diet, nutrition and the skin, Human Health Handbooks No. 2. 2012, pp. 318-331. DOI 10.3920/978-90-8686-729-5_19 (Year: 2012).*
International Search Report for PCT/EP2018/067337, dated Oct. 4, 2018, 4 pages.
Written Opinion of the International Searching Authority for PCT/EP2018/067337, dated Oct. 4, 2018, 6 pages.
Masako et al., "A Novel method to control the balance of skin microflora. Part I", J. Dermatological Sci. 2005, 38(3), 197-205.
Masako et al., "A Novel method to control the balance of skin microflora. Part II", J. Dermatological Sci. 2005, 38(3), 207-213.
Al-Ghazzewi et al., "Impact of prebiotics and probiotics on skin health", Beneficial Micr. 2014, 5(2), 99-107.

* cited by examiner

*Primary Examiner* — Yin-Horng Shiao

(57) ABSTRACT

The invention relates to topical formulations comprising: a galactooligosaccharide; 0.01% to 10% w/w xylitol; and a pharmaceutically or cosmetically acceptable carrier. The invention also relates to use of the formulations, and methods for their preparation.

10 Claims, No Drawings

US 11,234,997 B2

ANTIBACTERIAL ACTIVITY OF GALACTOOLIGOSACCHARIDE AND XYLITOL IN DERMATOLOGICAL TREATMENTS

CROSS-REFERENCE TO RELATED APPLICATIONS

This application is a U.S. national stage filing under 35 U.S.C. § 371 of International Patent Application PCT/EP2018/067337, filed on Jun. 27, 2018, which claims the benefit of the filing date of U.S. Provisional Patent Application Ser. No. 62/525,489, filed on Jun. 27, 2017. The contents of each of the preceding are hereby incorporated by reference in their entireties.

FIELD OF THE INVENTION

This invention relates to a topical formulation comprising a galactooligosaccharide and xylitol and its use in therapy by topical application.

BACKGROUND OF THE INVENTION

The largest organ of human body is the skin, which plays a pivotal role in protecting the host from pathogenic infections and penetration of harmful agents. Before birth, the skin is completely sterile but after birth, environmental microbes that are in homeostasis with the host colonize it. Moreover, after a vaginal delivery, fecal and vaginal microbes belonging to the mother's bacterial microflora also colonize the skin of infants. The microbial community living on the human skin is called skin microbiota, and it is constituted by over 100 distinct species of bacteria. The skin is the body's interface to the outside world, and it harbors populations of non-pathogenic, commensal microorganisms have an important function in skin health and disease.

Our skin hosts about $10^6$ bacteria per square centimeter which form our skin microflora. A healthy balanced skin biota is the microbial shield against pathogenic microorganisms and it can prevent dry skin conditions and improve skin health.

Alterations in the skin microbiome are an important component of the pathophysiology of atopic dermatitis. Skin affected by atopic dermatitis is often colonized by *Staphylococcus aureus* (*S. aureus*), particularly during a disease flare, whereas the abundance of other commensal bacteria is markedly decreased. These changes in the skin microbiome negatively affect the epidermal barrier and initiate inflammation. When bacteria such as *S. aureus*, attach to the skin surface, they form biofilms which act as a scaffold for further bacterial growth. Antibiotics are not the optimal treatment for removing bacteria from the skin of atopic dermatitis patients due to issues such as skin irritation and bacterial resistance.

It is an object of the present invention to provide a topical formulation for treating a skin disease or disorder, for example atopic dermatitis.

SUMMARY OF THE INVENTION

In a first aspect, the invention provides a topical formulation comprising:
a galactooligosaccharide;
0.01% to 10% w/w xylitol; and
a pharmaceutically or cosmetically acceptable carrier.

In a second aspect, the invention provides the formulation as defined by the first aspect of the invention for use in therapy.

In a third aspect, the invention provides a formulation comprising:
a galactooligosaccharide,
xylitol, and
a pharmaceutically or cosmetically acceptable carrier
for use in therapy by topical application.

In a fourth aspect, the invention provides the formulation as defined by the first aspect of the invention for use as a cosmetic.

Surprisingly, the applicant has found that a formulation comprising galactooligosaccharide and xylitol has a beneficial effect on the skin microbiome and thereby is suitable for treating diseases and disorders of the skin and for cosmetic uses to improve the appearance of the skin.

In a fifth aspect, the invention provides a topical formulation comprising a galactooligosaccharide for use in treating atopic dermatitis by topical application.

Additional aspects of the invention are more fully described in the following detailed description of the various embodiments.

DETAILED DESCRIPTION OF THE INVENTION

The invention provides a topical formulation comprising:
a galactooligosaccharide;
0.01% to 10% w/w xylitol; and
a pharmaceutically or cosmetically acceptable carrier.

The topical formulation includes a galactooligosaccharide. For the avoidance of doubt, the term galactooligosaccharide includes mixtures (i.e. one or more) galactooligosaccharides, and formulations comprising mixtures of galactooligosaccharides are covered by the invention.

Galactooligosaccharides belong to the group of prebiotics, which are non-digestible food ingredients that beneficially affect the host by stimulating the growth and/or the activity of beneficial bacteria. Galactooligosaccharide is present in commercially available products such as food for both infants and adults. Galactooligosaccharides are produced through the enzymatic conversion of lactose or from a botanical source, and its composition of the galactooligosaccharide fraction varies in chain length and type of linkage between the monomer units.

Galactooligosaccharides are oligomers or polymers of galactose molecules ending mainly with a glucose or sometimes ending with a galactose molecule and have varying degrees of polymerization and types of linkages. In one embodiment, galactooligosaccharide comprises galactose and glucose molecules. In another embodiment, galactooligosaccharide comprises only galactose molecules. In a further embodiment, galactooligosaccharide are galactose-containing oligosaccharides of the form of $[\beta\text{-D-Gal-}(1\text{-}6)]_n\text{-}\beta\text{-D-Gal-}(1\text{-}4)\text{-D-Glc}$ wherein n is 2-20. In another embodiment, the galactooligosaccharide are galactose-containing oligosaccharides of the form $\text{Glc-}\alpha\text{-}1\text{-}4\text{-}\beta\text{-Gal}1\text{-}6]_n$ where n=2-20. In another embodiment, the galactooligosaccharides are in the form of $\alpha\text{-D-Glc}(1\text{-}4)\text{-}[(\beta\text{-D-Gal-}(1\text{-}6)]_n$, where n=2-20. Gal is a galactopyranose unit and Glc (or Glu) is a glucopyranose unit.

Galactooligosaccharides are found in human and bovine maternal milk. Galactooligosaccharides can be produced from lactose syrup using the transgalactosylase activity of the enzyme .beta.-galactosidase (Crittenden, (1999) Probiotics: A Critical Review. Tannock, G. (ed) Horizon Scientific Press, Wymondham, pp. 141-156). β-D-galactosidase is known to catalyze not only the hydrolysis of the β-D-galactoside linkage of lactose to give D-glucose and D-galactose but also to carry out transgalactosylation reactions where the D-galactosyl group of a .beta.-D-galactoside is transferred onto a hydroxylated acceptor. For example, when a β-D-galactoside such as lactose or another carbohydrate is present, it is possible to obtain new glycoside linkages between the D-galactose unit and the acceptor. The starting galactoside such as lactose can also be present in a galactooligosaccharide mixture following the transgalactosylation reactions.

As used herein, galactooligosaccharide comprises one or more saccharides that have been produced from a glycoside and the transgalactosylation reaction of a β-galactosidase. Thus, galactooligosaccharides include saccharides such as transgalactosylated oligosaccharides (i.e. transgalacto-oligosaccharides) or transgalactosylate disaccharides. The degrees of polymerization (DP) of the formed oligosaccharide can vary, typically from 2-20, depending on the enzyme source. In one embodiment, a galactooligosaccharides composition is a blend of one more saccharides with a DP range of 2-6 (i.e. di- through hexasaccharides).

In another embodiment, a galactooligosaccharides composition is a blend of one or more saccharides with a DP range of 2-8 (i.e. di- through octa-saccharides). In another embodiment, a galactooligosaccharide composition is a blend of one or more saccharides with a DP range of greater than 8. In yet another embodiment, a galactooligosaccharides composition is a blend of one or more saccharides with a DP range of 9-15. In another embodiment, a galactooligosaccharides composition is a blend of one or more saccharides with a DP of 1, a DP range of 2-6, a DP range of 6-8, and DP range of greater than 8.

In one embodiment, the topical formulation comprises 0.01% to 10% w/w galactooligosaccharide, for example 0.01% to 5% w/w galactooligosaccharide. Alternatively, the formulation comprises 0.1% to 5% w/w galactooligosaccharide or 0.5% to 5% w/w galactooligosaccharide.

In a preferred embodiment, the topical formulation comprises 0.01% to 5% w/w galactooligosaccharide.

The topical formulation includes 0.01% to 10% w/w xylitol. Xylitol is a naturally occurring sugar alcohol used as a sweetener. It is found in low concentrations in the fibers of many fruits and vegetables and can be extracted from various berries, oats, and mushrooms, as well as fibrous material such as cornhusks and sugar cane bagasse.

In one embodiment, the topical formulation comprises 0.01% to 5% w/w xylitol. Alternatively, the formulation comprises 0.1% to 5% w/w xylitol or 0.5% to 5% w/w xylitol.

In a preferred embodiment, the topical formulation comprises 0.01% to 5% w/w xylitol.

In one embodiment, the topical formulation comprises a weight ratio of galactooligosaccharide:xylitol of from 10:1 to 1:10, from 8:1 to 1:8, from 5:1 to 1:5, or from 3:1 to 1:3.

In a preferred embodiment, the topical formulation comprises a weight ratio of galactooligosaccharide:xylitol of from 2:1 to 1:2.

The topical formulations are for use in therapy, in particular by topical application.

In one embodiment, the invention provides a topical formulation comprising:
 a galactooligosaccharide;
 xylitol; and
 a pharmaceutically or cosmetically acceptable carrier;
for use in therapy by topical application.

In a further embodiment, the invention provides a topical formulation comprising a galactooligosaccharide for use in treating atopic dermatitis by topical application.

In one embodiment, the formulations are for use in the treatment of a skin disease or disorder.

In one embodiment, the invention provides a method of treating a skin disease or disorder comprising the topical application of an effective amount of topical formulation according to the invention to a patient in need thereof.

In another embodiment, the invention provides the use of a galactooligosaccharide and xylitol for the manufacture of a medicament for use in a method of treating a skin disease or disorder.

In one embodiment, the topical formulations are for use in the treatment of a skin disease or disorder associated with *S. aureus*. A skin disease or disorder associated with *S. aureus* is one which is caused or promoted by *S. aureus*.

*S. aureus* is a gram-positive pathogenic strain responsible for a wide variety of conditions, ranging from clinical inflammation to severe infections causing pneumonia, endocarditis and septicaemia. *S. aureus* is one of the most important bacteria in human diseases. *S. aureus* is particularly associated with atopic dermatitis, a common chronic inflammatory skin disease characterized by acute eczematous lesions erythema. Pruritus is also prominent and consistent and thus has an effect on quality of life. Atopic dermatitis affects 10-30% of children and 2-3% of adults in industrialized countries. *S. aureus* is also a causative or compounding factor in the pathogenesis of other minor skin infections such as pimples, impetigo, cellulitis and folliculitis, and in more serious and invasive diseases such as pneumonia, vaginitis, meningitis, osteomyelitis, toxic shock syndrome, bacteraemia, and sepsis.

In one embodiment, the skin disease or disorder is atopic dermatitis (i.e. atopic eczema), and in particular is atopic dermatitis associated with *S. aureus*.

Without being bound by theory, it is thought that the topical formulations of the invention promote growth of *Staphylococcus epidermidis* (*S. epidermidis*), the most commonly isolated bacteria species in healthy skin which makes up to 90% of the aerobic flora. *S. epidermidis* balances the inflammatory response after skin injury and produces antimicrobial molecules selectively inhibiting skin pathogens. The growth of *S. epidermidis* is thought to inhibit growth of *S. aureus*.

Accordingly, the invention provides the use of a topical formulation of the invention for preventing the growth of *S. aureus*, in particular on the skin of a human or animal.

Again without being bound by theory, it is thought that the topical formulations of the invention prevent the formation of a biofilm of *S. aureus* or remove such a biofilm once formed, in particular on the skin of a human or animal.

Accordingly, the invention provides the use of a topical formulation of the invention for preventing the formation of a biofilm of *S. aureus* or removing such a biofilm once formed, in particular on the skin of a human or animal.

In another embodiment, the invention provides the use of the topical formulation as a cosmetic. In the cosmetic use of the invention, the topical formulation is not used in therapy. Rather, the formulation is used to improve the appearance of the surface e.g. skin to which the formulation is topically applied.

Another aspect of the present invention is a method for the preparation of the topical formulation comprising galactooligosaccharide. In one embodiment, the method involves mixing the galactooligosaccharide, xylitol and the pharmaceutically or cosmetically acceptable carrier, and then isolating the topical formulation.

The topical formulation is for topical application. The topical formulation can be a dermatological formulation.

Preferably the topical formulation is applied to the skin. Accordingly, the topical formulations typically in liquid or semi-solid form, for example as an emulsion (e.g. an oil-in-water emulsion or a water-in-oil emulsion), an emollient, a paste, a cream, an ointment, a gel, a shampoo or a wipe.

Accordingly, the formulation also comprises a pharmaceutically or cosmetically acceptable carrier of the sort suitable for applications intended for topical application.

The topical formulation is preferably an oil-in-water emulsion comprising an oil, at least one surfactant-emulsifier, galactooligosaccharide, xylitol, and water.

The oil is a generally a mineral oil. The emulsion comprises other ingredients which are typically present in oil-in-water emulsions. For example, the formulation of the invention may optionally contain a moisture protecting agent, such as glycerin. This formulation may also contain a fatty acid alcohol, e.g., stearyl alcohol, palmityl alcohol, maleic alcohol or cetyl alcohol. The present formulation also contains an aqueous medium, e.g. generally purified water.

The fatty acid may have a maximum of 16 to 18 carbons, for example stearate and palmitate, among others. Optional enhancers may be included, for example, citrate, maleic acid, ethylenediaminetetraacetic acid, free amino acids and carbopol, xanthan gum, carrageenan, and conditioning quaternarized polymers.

Additionally, it is desirable to include a small amount of preservative in the formulation of the present invention to enable storage of the formulations in good condition. Preservatives such as methyl and propyl paraben may be employed, as well as other known preservatives like, phenoxyethanol, sodium benzoate, and potassium sorbate. Formulations can be preserved using also pentylene glycol, decylene glycol, 1,2-octanediol, 1,2-hexanediol, and o-Cymen-5-ol.

Additionally, it is desirable to include surfactants in the formulation of the present invention. The formulation can contain sodium laureth sulphate, sodium myreth sulphate, disodium laureth sulfosuccinate, sodium cocoamphoacetate, and sodium cocoamphoacetate.

Depending upon the specific formulation of the formulation the other ingredients or excipients will vary in their functionality and amount. For example, in addition to galactooligosaccharide and xylitol, body wash, body lotion, emollients and body wash formulations typically contain the following amounts of excipients.

| Body lotion (amount % w/w) | |
|---|---|
| Water | 55-70 |
| Emollient | 5-20 |
| Conditioner | 5-10 |
| Humectant | 0.1-10 |
| Surfactant | 0.1-3 |
| Fragrance | 0.1-2 |
| Antioxidant | 0.1-2 |
| Stabilising agent | 0.1-5 |
| Viscosity controller | 0.1-2 |
| Gelling agent | 0.1-2 |
| Emulsifier | 0.1-2 |
| Absorbent | 0.1-2 |
| Buffer | 0.01-0.5 |

| Body wash (amount % w/w) | |
|---|---|
| Water | 75-90 |
| Surfactant | 5-10 |
| Humectant | 0.1-5 |
| Conditioner | 0.1-5 |
| Fragrance | 0.1-2 |
| Emollient | 0.1-2 |
| Gelling agent | 0.1-2 |
| Preservative | 0.1-2 |
| Buffer | 0.1-2 |

| Shampoo (amount % w/w) | |
|---|---|
| Water | 80-95 |
| Surfactant | 5-12 |
| Humectant | 0.1-5 |
| Conditioner | 0.1-2 |
| Fragrance | 0.1-2 |
| Emollient | 0.1-2 |
| Antioxidant | 0.1-2 |
| Antimicrobial | 0.1-2 |
| Buffer | 0.1-2 |
| Chelating agent | 0.01-0.5 |

| Emollient (amount % w/w) | |
|---|---|
| Water | 50-70 |
| Emollient | 5-15 |
| Humectant | 5-15 |
| Conditioner | 5-15 |
| Emulsifier | 1-10 |
| Stabilising agent | 0.1-5 |
| Antioxidant | 0.1-2 |
| Gelling agent | 0.1-2 |
| Chelating agent | 0.1-2 |
| Masking agent | 0.1-2 |
| Buffer | 0.01-0.5 |

The formulations according to the invention are stable, and exhibit good physical and chemical stability over time, even at a temperature above ambient temperature.

In another embodiment, the topical formulation is supplied on a wipe. In this embodiment, the user can topically apply the formulation using the wipe.

The following examples describe the successful inhibition of *S. aureus* with the formulations of the invention, and therefore indicate that the topical formulations would be useful for treating skin diseases and disorders, in particular atopic dermatitis.

EXAMPLES

Example 1

The following topical formulation is a skin cleanser.

| | % w/w |
|---|---|
| Potassium Glycyrrhizinate | 0.1-0.5 |
| Niacinamide | 0.1-1 |

-continued

| | % w/w |
|---|---|
| Xylitol | 5 |
| Galactooligosaccharides | 0.5 |
| Xanthan gum | 0.1-0.5 |
| Caprylic/capric triglyceride | 4 |
| *Glycine soya* (soyabean) sterols | 0.1-1 |
| Glycosphingolipids, phospholipids, cholesterol | 0.1-0.5 |
| BHT | 0.05-1 |
| Polyglyceryl-6 distearate (and) jojoba esters(and) polyglyceryl-3 beeswax (and) cetyl alcohol | 3-5 |
| Isoamyl laurate | 1-3 |
| Potassium cetyl phosphate, hydrogenated palm glycerides | 0.4-1 |
| Laureth-9 | 1-3 |
| Glyceryl laurate | 1-3 |
| Cetearylalcohol | 1-3 |
| *Butyrospermum parkii* | 5-10 |
| Hydrogenated lecithin | 0.1-3 |
| Stearyl glycyrrhetinate | 0.1-05 |
| *Linum usitatissimum* seed oil | 2-5 |
| Tocopheryl Acetate | 1-4 |
| Acrylates/C10-30 alkyl acrylate crosspolymer | 0.1-2 |
| Methylpropandiol, caprylyl glycol, phenylpropanol | 1-4 |
| Arginine | 1-3 |
| Water | to 100 |

Example 2

The following topical formulation is an emollient:

| | % w/w |
|---|---|
| Xylitol | 5 |
| Disodium laureth sulfosuccinate | 5-15 |
| Laureth-9 | 1-3 |
| Sodium cocoamphoacetate | 1-15 |
| Hydroxypropyl guar hydroxypropyltrimonium chloride | 0.5-4 |
| Lactic acid | |
| Caprylyl glycol | 0.5-3 |
| Sodium lauryl sulfoacetate | 1-5 |
| Propylene glycol | 1-5 |
| Niacinamide | 0.1-3 |
| Galactooligosaccharide | 0.5 |
| Dipotassium glycyrrhizate | 0.1-1 |
| *Malva sylvestris* flower/leaf/stem extract | 1-3 |
| Aqua/water | to 100 |

Approximately $1 \times 10^4$ cfu of two different strains of *S. aureus* (ATCC 29213 and 815) were added to the formulations of Examples 1 and 2. The results are expressed as the % of growth inhibition and biofilm formation inhabitation at 3 hours.

TABLE 1

| | Example 1 | | Example 2 | |
|---|---|---|---|---|
| *S. aureus* | ATCC 29213 | 815 | ATCC 29213 | 815 |
| Growth inhibition | 99.99% at 3 h | 99.99% at 3 h | 99.99% at 3 h | 100% at 3 h |
| Biofilm formation inhibition | 99.99% at 3 h | 99.99% at 3 h | 99.99% at 3 h | 99.99% at 3 h |

All formulations rapidly inhibited the growth of both *S. aureus* strains within 3 hours and inhibited the formation of biofilms. These results demonstrate the possibility of inhibiting the pathogenic skin microflora in skin disorders using preservative-free probiotic-containing formulations.

Example 3

Table 2 sets out typical amounts of galactooligosaccharide (GOS) and xylitol (w/w) of the formulation in particular types of formulation.

| Formulation | GOS % w/w | xylitol % w/w |
|---|---|---|
| Cleanser | 0.01-3 e.g 0.5 | 1-10 e.g. 5 |
| Emollient | 0.01-3 e.g 0.5 | 1-10 e.g. 5 |
| Body wash | 0.01-3 e.g 0.5 | 0.01-3 e.g 0.5 |
| Nappy rash cream | 0.5-2.5 e.g. 1 | 0.1-3 e.g. 1 |
| Moisturising cream | 0.1-3 e.g. 1 | 0.1-3 e.g. 1 |
| Wet wipes | 0.01-3 e.g. 0.1 | 0.01-3 e.g. 0.1 |
| Bath foam | 0.01-3 e.g. 0.1 | 0.01-3 e.g. 0.1 |
| Shampoo | 0.01-3 e.g. 0.1 | 0.01-3 e.g. 0.1 |
| Body lotion | 0.1-3 e.g. 1 | 0.1-3 e.g. 1 |

Example 4

Galactooligosaccharide and xylitol were evaluated alone and in combination at different concentrations (concentrations: 0, 1, 2.5 and 5%) to affect bacterial planktonic production and biofilm-forming ability of standardized broth cultures of *S. aureus* 815 (clinical strain) and *S. epidermidis* 317 (clinical strain) was assessed.

The planktonic form of bacteria is characterised by separated cells that independently float or exist as a suspension within liquid media. The biofilm (or aggregated/sessile) form is characterised by a state in which the cells are tightly constrained and firmly attached to one another. Typically the biofilm form is associated with clinical inflammation and infection in humans.

Example 4.1

Planktonic Phase

Different concentrations of galactooligosaccharide, xylitol and their combination, were added to a 96 well plate to evaluate their in vitro effect on *S. aureus* and *S. epidermidis* bacterial planktonic population. The overnight bacterial inocula were prepared in Tryptic soy broth (TSB), refreshed in the same medium and adjusted to $OD_{600}=0.12$ (approximately $5 \times 10^6$ CFU/ml) for the experiments. For the controls, galactooligosaccharide and xylitol were also assayed alone. The plates were incubated for t=3, and 6 h at 37° C. in aerobic conditions. Each determination was performed in duplicate for three independent experiments and the biomass was evaluated using a safranin staining method.

After each time of incubation, the reduction of the $OD_{600}$ was evaluated in respect to the controls and the colony forming units (CFU)/ml at 0 and 24 h were detected. Each determination was performed in duplicate for three independent experiments and the biomass was evaluated using a safranin staining method.

Table 3 outlines the percentage reduction of *S. aureus* 815 and *S. epidermidis* 317 growth in planktonic phase in the presence of galactooligosaccharide, xylitol and their combinations at different concentrations ($OD_{600}$) after 3 and 6 h.

| | | Xylitol (%) | | | |
|---|---|---|---|---|---|
| | | 0 | 1 | 2.5 | 5 |
| 3 h - *S. aureus* 815 | | | | | |
| GOS (%) | 0 | 0 | 14.38 | 23.93 | 26.70 |
| | 1 | 13.88 | 22.47 | 27.94 | 30.23 |
| | 2.5 | 18.78 | 26.80 | 32.24 | 34.96 |
| | 5 | 29.52 | 34.26 | 38.88 | 40.66 |
| 6 h - *S. aureus* 815 | | | | | |
| GOS (%) | 0 | 0 | 15.86 | 27.80 | 35.13 |
| | 1 | 22.59 | 34.54 | 41.18 | 43.60 |
| | 2.5 | 22.35 | 31.44 | 37.39 | 46.42 |
| | 5 | 32.26 | 41.88 | 51.35 | 55.50 |
| 3 h - *S. epidermidis* 317 | | | | | |
| GOS (%) | 0 | 0 | 13.40 | 19.36 | 27.13 |
| | 1 | 10.89 | 19.94 | 27.10 | 32.94 |
| | 2.5 | 20.94 | 32.16 | 34.57 | 38.81 |
| | 5 | 31.35 | 33.38 | 38.70 | 45.34 |
| 6 h - *S. epidermidis* 317 | | | | | |
| GOS (%) | 0 | 0 | 22.11 | 28.57 | 29.99 |
| | 1 | 15.92 | 27.86 | 37.78 | 42.89 |
| | 2.5 | 26.63 | 34.75 | 40.18 | 45.87 |
| | 5 | 36.67 | 40.41 | 45.70 | 51.06 |

Galactooligosaccharide and xylitol dosed alone and in combination provide a reduction in the planktonic growth of both *S. aureus* 815 and *S. epidermidis* 317.

Example 4.2

Biofilm Phase

Bacterial suspensions grown in TSB supplemented with 0.5% (v/v) glucose at logarithmic phase, were incubated on 96 flat-bottomed microliter plates in the presence of galactooligosaccharide or xylitol or their combination at different concentrations or TSB (control). After incubation for 3 h and 24 h at 37° C., each well was washed twice with sterile PBS, air-dried, stained for 1 min with 0.1% safranin, and washed with PBS. The stained biofilm were re-suspended in 200 µl ethanol (95% v/v), and $OD_{492}$ was measured by spectrophotometry using an ELISA reader.

Table 4 outlines the percentage of biofilm reduction (anti-adhesive (3 h) and anti-biofilm (24 h)) of *S. aureus* 815 and *S. epidermidis* 317 in the presence of galactooligosaccharide, xylitol and their combinations at different concentrations.

| | | Xylitol (%) | | | |
|---|---|---|---|---|---|
| | | 0 | 1 | 2.5 | 5 |
| 3 h - *S. aureus* 815 | | | | | |
| GOS (%) | 0 | 0 | 21.61 | 28.81 | 36.98 |
| | 1 | 16.66 | 29.44 | 33.15 | 38.45 |
| | 2.5 | 21.02 | 25.62 | 31.47 | 35.36 |
| | 5 | 28.16 | 29.97 | 35.89 | 39.60 |
| 24 h - *S. aureus* 815 | | | | | |
| GOS (%) | 0 | 0 | 51.68 | 47.8 | 56.02 |
| | 1 | 38.59 | 35.94 | 48.94 | 51.53 |
| | 2.5 | 40.88 | 33.76 | 39.79 | 61.13 |
| | 5 | 32.14 | 33.93 | 36.07 | 50.03 |
| 3 h - *S. epidermidis* 317 | | | | | |
| GOS (%) | 0 | 0 | 1.00 | 10.64 | 14.16 |
| | 1 | 2.56 | 2.50 | 11.73 | 11.16 |
| | 2.5 | 1.20 | 2.84 | 13.83 | 14.86 |
| | 5 | 1.00 | 3.45 | 18.65 | 19.77 |
| 24 h - *S. epidermidis* 317 | | | | | |
| GOS (%) | 0 | 0 | 22.81 | 22.18 | 5.67 |
| | 1 | 4.70 | 8.34 | 18.02 | 11.50 |
| | 2.5 | 8.13 | 4.64 | 1.33 | 21.05 |
| | 5 | 8.76 | 8.30 | 12.49 | 13.69 |

Galactooligosaccharide and xylitol dosed alone and in combination provide a reduction of biofilm formation in *S. aureus* 815 up to 40% after 3 h of treatment (anti-adhesive effect) and up to 60% after 24 h (anti-biofilm effect). For *S. epidermidis* 317, this effect was not observed.

The present invention also includes the following embodiments:

1. A method for improving antibacterial efficacy against *S. Aureus* comprising the topical application of a dermatological formulation which comprises a Galactooligosaccharide.

2. The method wherein the formulation further comprises xylitol.

3. The method wherein the dermatological formulation is formulated as an emollient, detergent, paste, or gel.

4. The method wherein the galactooligosaccharide is present in an amount of 0% to 5% w/w of the formulation.

5. The method wherein the xylitol is present in an amount of 0% to 5% w/w of the formulation.

6. A method for improving antibacterial efficacy against *S. Aureus* comprising the topical application of a dermatological formulation which comprises from 0% to 5% w/w of the formulation of galactooligosaccharide and from 0% to 5% w/w of the formulation of xylitol.

7. A dermatological formulation which comprises from 0% to 5% w/w of the formulation of galactooligosaccharide and from 0% to 5% w/w of the formulation of xylitol.

8. A method for the treatment of atopic dermatitis, comprising topically applying onto the skin of an individual in need of such treatment, a topical composition comprising an effective amount of galactooligosaccharide.

9. The method wherein the composition is formulated as an emulsion.

The invention claimed is:

1. A topical formulation comprising:
   a galactooligosaccharide;
   0.01% to 10% w/w xylitol; and
   a pharmaceutically or cosmetically acceptable carrier,
   wherein a weight ratio of galactooligosaccharide:xylitol is from 10:1 to 1:10, and
   wherein the weight ratio is obtained by reducing preferentially biofilm of *Staphylococcus aureus* over *Staphylococcus epidermidis*.

2. The topical formulation as claimed in claim 1, wherein the xylitol component is present in an amount of 0.01% to 5% w/w xylitol.

3. The topical formulation of claim 1, wherein the galactooligosaccharide component is present in an amount of 0.01% to 10% w/w galactooligosaccharide.

4. The topical formulation of claim 1, wherein the galactooligosaccharide component is present in an amount of 0.01% to 5% w/w galactooligosaccharide.

5. The topical formulation of claim 1, wherein the weight ratio of galactooligosaccharide:xylitol is from 2:1 to 1.2.

6. The topical formulation of claim 1, wherein the formulation is an emulsion, an emollient, a paste, a cream, an ointment, or a gel.

7. A method for the treatment of a skin disease or disorder comprising,
  topically applying a formulation comprising a galactooligosaccharide; xylitol; and a pharmaceutically or cosmetically acceptable carrier;
  to a surface of the skin of a person in need of such treatment,
  wherein a weight ratio of galactooligosaccharide:xylitol is from 10:1 to 1:10 and wherein the weight ratio is obtained by reducing preferentially biofilm of *Staphylococcus aureus* over *Staphylococcus epidermidis*.

8. The method of claim 7, wherein the skin disease or disorder is a disease or disorder caused or promoted by *S. aureus*.

9. The method of claim 7, wherein the skin disease or disorder is atopic dermatitis.

10. A method for improving the appearance of the surface of skin comprising,
  topically applying a formulation comprising a galactooligosaccharide; xylitol; and a pharmaceutically or cosmetically acceptable carrier;
  to a surface of the skin of a person in need thereof,
  wherein a weight ratio of galactooligosaccharide:xylitol is from 10:1 to 1:10 and wherein the weight ratio is obtained by reducing preferentially biofilm of *Staphylococcus aureus* over *Staphylococcus epidermidis*.

* * * * *